United States Patent [19]

Gustke et al.

[11] Patent Number: 5,376,124
[45] Date of Patent: Dec. 27, 1994

[54] COLLARED HIP PROSTHESIS WITH REVISION SPACER

[75] Inventors: Kenneth A. Gustke, Tampa, Fla.; Kenneth J. Gardner, Roundrock; James E. Williams, Austin, both of Tex.

[73] Assignee: Intermedics Orthopedics, Inc., Austin, Tex.

[21] Appl. No.: 101,421

[22] Filed: Aug. 3, 1993

[51] Int. Cl.$^5$ .............................................. A61F 2/36
[52] U.S. Cl. .................................... 623/23; 623/18
[58] Field of Search ............... 623/16, 17, 18, 19, 623/20, 22, 23

[56] References Cited

U.S. PATENT DOCUMENTS

| | | | |
|---|---|---|---|
| 2,781,758 | 2/1957 | Chevalier | 623/23 |
| 2,785,673 | 3/1957 | Anderson | 623/23 |
| 4,012,796 | 3/1977 | Weisman et al. | 623/23 |
| 4,698,063 | 10/1987 | Link et al. | 623/23 |
| 4,753,657 | 6/1988 | Lee et al. | 623/23 |
| 4,770,666 | 9/1988 | Averill | 623/23 |
| 4,783,192 | 11/1988 | Wroblewski et al. | 623/23 |
| 5,047,061 | 9/1991 | Brown | 623/23 |
| 5,057,101 | 10/1991 | Dorr et al. | 623/23 |
| 5,116,380 | 5/1992 | Hewka et al. | 623/23 |
| 5,201,769 | 4/1993 | Schutler | 623/23 |

FOREIGN PATENT DOCUMENTS 3406358 12/1984 Germany ................. 623/22

*Primary Examiner*—David Isabella
*Attorney, Agent, or Firm*—John R. Merkling

[57] ABSTRACT

A spacer to be used with femoral hip prostheses. The spacer is placed under a existing collar of a femoral hip prosthesis and cemented or tied in place or both. The spacer comprises a U-shaped segment adapted to fit under a medial collar and partially enclose part of a proximal portion of the stem of a hip prosthesis. Spacer plugs are provided to offset the spacer slightly and provide a space which is filled with bone cement (PMMA), securely attaching the spacer to the prosthesis. A distal ledge which lies adjacent the proximal body of the prosthesis keeps the cement enclosed between the stem and the spacer. An area of porous coating is provided distally. A peripheral groove is also provided.

18 Claims, 2 Drawing Sheets

COLLARED HIP PROSTHESIS WITH REVISION SPACER

BACKGROUND OF OUR INVENTION

Our invention relates to femoral hip prosthesis and in particular to a spacer which can be placed under a collar on a femoral hip prosthesis to compensate for inadequate bone mass, particularly in revision surgeries.

Various types of femoral hip prosthesis are known and are used for surgical reconstruction of the femur. In general, these prostheses comprise a ball-shaped head mounted at an anatomical angle on a shank. The shank can be thrust into the medullar canal of a femur to mount the prosthesis on a resected surface of the femur. Many of these prostheses have collars near their proximal end which rest upon the resected surface. Both permanently attached, or integral, collars and replaceable collars are known.

In some cases, however, a patient's femur may have insufficient bone mass near the proximal end of the femur to support the collar or, during the revision surgery when a second operation is necessary, additional bone may be removed. To restore the prosthesis to an anatomically correct position, the prosthesis would protrude further out of the remaining femur, leaving a gap between the collar and the resected surface of the femur.

SUMMARY OF OUR INVENTION

Our invention relates to a spacer to be used in the situations described above. The spacer is placed under a existing collar and cemented or tied in place or both. This effectively brings the collar of the prosthesis into contact with a resected surface of a femur through the spacer. The spacer comprises a U-shaped segment adapted to fit under a medial collar and partially enclose part of a proximal portion of the stem of a hip prosthesis. Spacer plugs are provided to offset the spacer slightly and provide a space which is filled with bone cement (PMMA), securely attaching the spacer to the prosthesis. A distal ledge which lies adjacent the proximal body of the prosthesis keeps the cement enclosed between the stem and the spacer. An area of porous coating is provided distally on the spacer to permit bony ingrowth, if the implantation is a cementless one, or to accommodate cement interdigitation. A peripheral groove is provided so that the spacer may optionally be tied to the proximal body of the hip prosthesis with a surgical wire.

With the foregoing in mind, it is an object of our invention to provide a femoral hip prosthesis with an optional spacer which can be applied to bring a proximal collar on the prosthesis in contact with available bone.

Further object of our invention is to provide a spacer which can be used with a hip prosthesis and secured thereto by bone cement or mechanical means.

These and other objects and advantages of our invention will become apparent from the following detailed description taken in conjunction with the accompanying drawings.

DETAILED DESCRIPTION OF OUR PREFERRED EMBODIMENT

Figure 1:
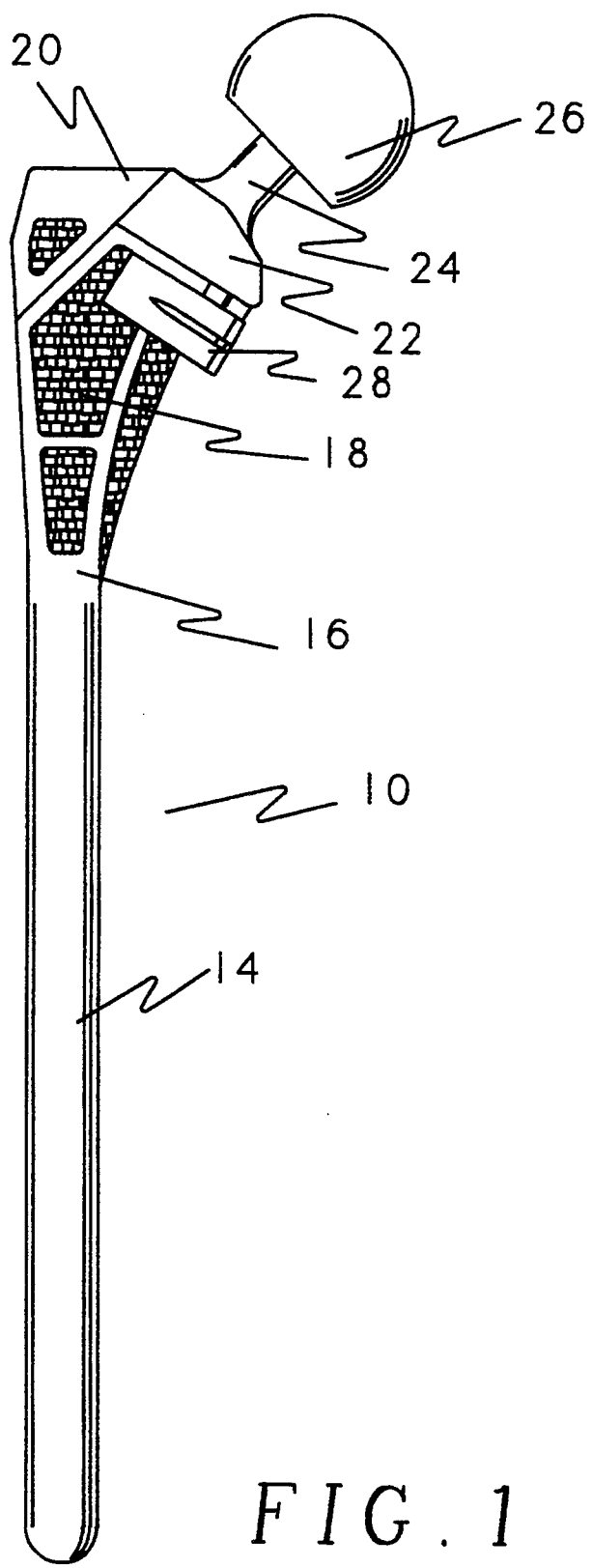
FIG. 1 is a plan view of a femoral prosthesis with a spacer in accordance with our invention.

In referring to the accompanying drawings, like numerals will refer to like parts throughout the description. In FIG. 1, a femoral hip prosthesis 10 is shown. We have illustrated a revision prosthesis but our invention could also be used with primary prostheses, such a the prosthesis described in U.S. Pat. No. 5,057,101 to Dorr, et al. The hip prosthesis 10 has a distal shank 14 which is inserted into the medullary canal of a patient's femur. Matching the general configuration of the medullary canal, this shaft is usually circular in cross-section and may be curved, particularly in the anterior-posterior plane. A proximal body 16 of the prosthesis fills a proximal portion of the femur with a more rectangular cross-section. Various techniques for reaming and otherwise shaping the interior of the femur to receive a prosthesis are known in the art. In our preferred embodiment an area of porous coating 18 is provided on the proximal body 16. In cement free implantation of hip prosthesis, the porous area 18 encourages bony ingrowth, securing the proximal part of the prosthesis of the femur. In cemented applications, bone cement will, at least to some extent, enter the pores of a porous surface, also providing an enhanced degree of fixation. At proximal end 20 of the prosthesis 10 a collar 22 is provided. The collar 22 is intended to rest on a resected proximal surface of the femur, supporting the prosthesis against subsidence into the medullar canal. On the proximal end 20 of the prosthesis, there is a neck 24 which supports a generally spherical, polished head 26. As is known in this art, the head 26 may be either integral with the neck or releasably mounted thereon, for example by a taper lock. The head 26 articulates either with the natural acetabular surface, if it is still healthy, or with an artificial acetabular prosthesis (not shown).

Figure 2:
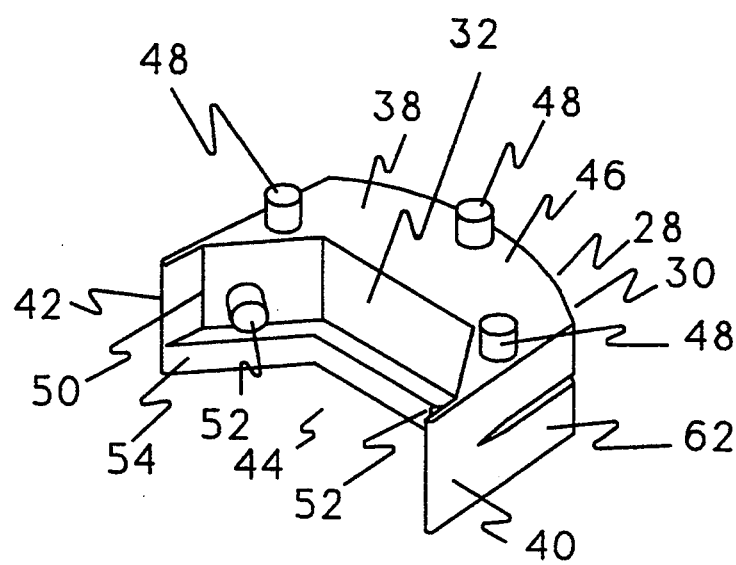
FIG. 2 is a prospective top view of the spacer of FIG. 1.

Under the collar 22 there is an optional spacer 28 which may be placed under the collar and against the proximal body 18 to accommodate those situations where the proximal portion of the femur must be cut away to provide adequate healthy bone mass for supporting the prosthesis. Clearly, to accommodate different situations, spacers of differing widths are contemplated. The configuration of the spacer will be more fully understood by reference to FIGS. 2 through 4.

Spacer 28 comprises a generally U-shaped body 30 having a central portion 32 and opposed arms 40, 42. The arms 40, 42 form a cavity 44 which wraps partially around the proximal body of the prosthesis. A proximal surface 46 is configured to lie adjacent the collar 22. The spacer 28 is held away from the collar by buttons 48 on the proximal surface 46. These buttons are preferably PMMA and provide a space which can be filled with PMMA bone cement to attach the spacer to the prosthesis prior to implantation.

Figure 3:
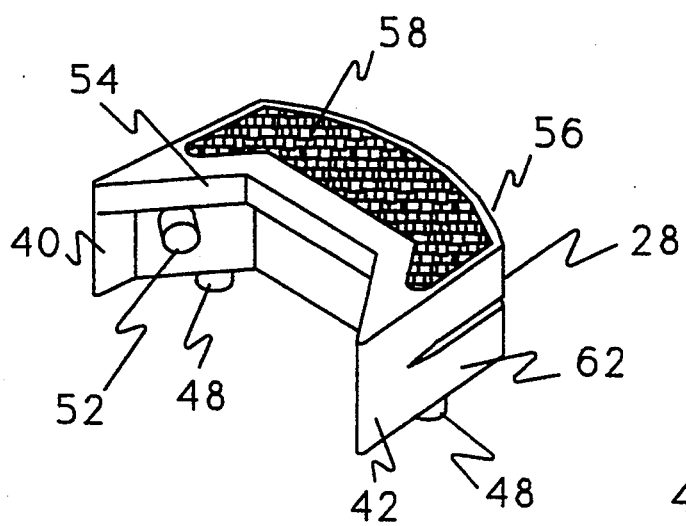
FIG. 3 is a prospective bottom view of the spacer of FIG. 2.
Figure 4:
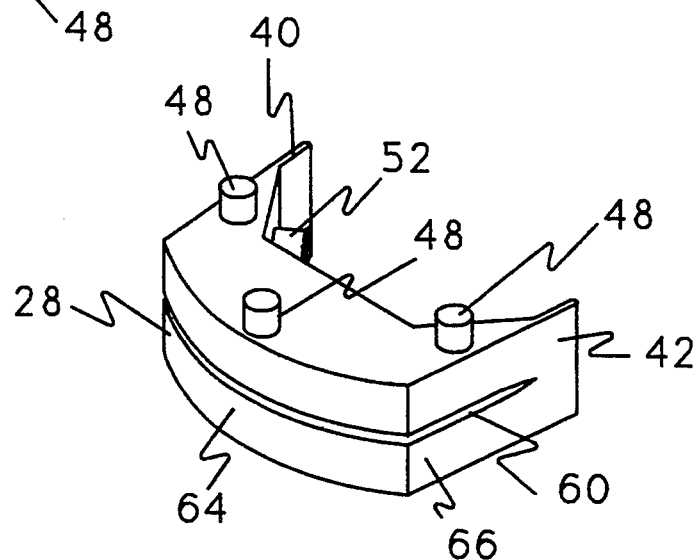
FIG. 4 is a reverse top view of the spacer of FIG. 2.

Similarly, an inner surface 50 surrounds the cavity 44 and faces the proximal body of the prosthesis. Buttons 52 are provided for the same purpose as the buttons 48. A distal ledge 54 is located distally on the surface 50. This ledge tends to capture the bone cement above it and hold the cement between the spacer and the proximal body and collar of the hip prosthesis until the cement has set. As seen in FIG. 3, a distal side 56 of the spacer 28 has a region of porous coating 56. If the prosthesis and spacer combination are implanted in the femur without bone cement as a fixation medium, the porous area 58 will promote fixation by encouraging bony ingrowth from the resected surface of the femur. Where cement is used as a fixation medium, some interdigitation of the bone cement into the porous area can be expected, providing enhanced fixation.

The spacer may also be secured to the proximal body of the prosthesis 10 by surgical wire passed around the spacer and around the lateral side of the prosthesis. To aid such an attachment, we have a provided a peripheral groove 60 on faces 62, 64, and 66 which are away from the proximal body of the prosthesis.

Our invention may be embodied in other specific forms without departing from the spirit or essential characteristics thereof. The present embodiment is therefore considered in all aspects as illustrative and not restrictive, the scope of our invention being indicated by the appended claims rather by the foregoing description, and all changes which come within the meaning and range of equivalency of the claims are therefore intended to be embraced therein.

We claim as our invention:

1. A spacer for a femoral component of a prosthetic hip, said femoral component having a proximal body, a stem distal therefrom, a neck proximal from said proximal body for receiving a ball, and a collar between said proximal body and said neck at at least a lateral side of said proximal body, said spacer comprising
   a generally U-shaped body adapted to be placed under said collar, said body having
   a central portion with a surface adapted to lie adjacent said proximal body in spaced relationship thereto,
   a ledge forming a lip protruding from said surface on said central portion towards said femoral component along at least a distal edge of said surface on said central portion, and
   two opposed arms on anterior and posterior ends of said central portion, each of said arms having a surface adapted to lie adjacent said proximal body in spaced relationship thereto, said ledge and said surfaces on said portion along with said arms forming a cavity between said proximal body and said spacer for receiving means for cementing said spacer to said femoral component.

2. The spacer according to claim 1 herein said ledge forming a protruding lip also extends along distal edges on said surfaces on said arms.

3. The spacer according to claim 2 further comprising at least one button on said spacer and adapted to contact said femoral component for maintaining said spacer in spaced relationship to said femoral component.

4. The spacer according to claim 3 further comprising means for mechanically securing said spacer to said proximal body.

5. The spacer according to claim 4 wherein said means for mechanically securing comprise a peripheral groove on said spacer and a wire circumscribing said spacer and said proximal body.

6. The spacer according to claim 5 further comprising a area of porous material for fixation to adjacent bone or bone cement.

7. The spacer according to claim 1 further comprising a area of porous material for fixation to adjacent bone or bone cement.

8. The spacer according to claim 2 further comprising a area of porous material for fixation to adjacent bone or bone cement.

9. The spacer according to claim 1 further comprising at least one button on said spacer and adapted to contact said femoral component for maintaining said spacer in spaced relationship to said femoral component.

10. A prosthetic hip comprising a femoral component having
    a proximal body,
    a stem distal therefrom,
    a neck proximal from said proximal body,
    a ball connected to said neck, and
    a collar between said proximal body and said neck at at least a lateral side of said proximal body, and
    a spacer having a generally U-shaped body adapted to be placed under said collar, said body having
    a central portion with a surface adapted to lie adjacent said proximal body in spaced relationship thereto,
    a ledge forming a lip protruding from said central portion towards said femoral component along at least a distal edge of said surface on said central portion, and
    two opposed arms on anterior and posterior ends of said central portion, each of said arms having a surface adapted to lie adjacent said proximal body in spaced relationship thereto said ledge and said surfaces on said portion along with said arms forming a cavity between said proximal body and said spacer for receiving means for cementing said spacer to said femoral component.

11. The prosthetic hip according to claim 10 wherein said ledge forming a protruding lip also extends along distal edges on said surfaces on said arms.

12. The prosthetic hip according to claim 11 further comprising at least one button on said spacer and adapted to contact said femoral component for maintaining said spacer in spaced relationship to said femoral component.

13. The prosthetic hip according to claim 12 further comprising means for mechanically securing said spacer to said proximal body.

14. The prosthetic hip according to claim 13 wherein said means for mechanically securing comprise a peripheral groove on said spacer and a wire circumscribing said spacer and said proximal body.

15. The prosthetic hip according to claim 14 further comprising a area of porous material for fixation to adjacent bone or bone cement.

16. The prosthetic hip according to claim 10 further comprising a area of porous material for fixation to adjacent bone or bone cement.

17. The prosthetic hip according to claim 11 further comprising a area of porous material for fixation to adjacent bone or bone cement.

18. The prosthetic hip according to claim 10 further comprising at least one button on said spacer and adapted to contact said femoral component for maintaining said spacer in spaced relationship to said femoral component.

* * * * *